(12) United States Patent
Etridge et al.

(10) Patent No.: US 6,225,465 B1
(45) Date of Patent: May 1, 2001

(54) PROCESS FOR THE AMINOCARBONYLATION OF BENZAZEPINES AND BENZODIAZEPINES

(75) Inventors: Stephen K. Etridge, Maidstone; Timothy Charles Walsgrove, Tunbridge Wells; Jerome Hayes, Tunbridge Wells; Andrew S. Wells, Tunbridge Wells, all of (GB)

(73) Assignee: SmithKline Beecham plc, Brentford (GB)

( * ) Notice: Subject to any disclaimer, the term of this patent is extended or adjusted under 35 U.S.C. 154(b) by 0 days.

(21) Appl. No.: 09/091,966

(22) PCT Filed: Dec. 27, 1996

(86) PCT No.: PCT/IB96/01502

§ 371 Date: May 14, 1999

§ 102(e) Date: May 14, 1999

(87) PCT Pub. No.: WO97/24336

PCT Pub. Date: Jul. 10, 1997

Related U.S. Application Data

(60) Provisional application No. 60/009,531, filed on Dec. 29, 1995.

(51) Int. Cl.$^7$ .................. C07D 243/14; C07D 401/14; C07D 403/12; C07D 417/04; C07D 401/12
(52) U.S. Cl. .................. 540/504; 540/513; 540/593
(58) Field of Search .................. 540/504, 513, 540/593

(56) References Cited

U.S. PATENT DOCUMENTS 5,977,101 * 11/1999 Ali et al. .................. 514/221

FOREIGN PATENT DOCUMENTS

| 0 444 853 | 9/1991 | (EP) . |
| 0 504 695 | 9/1992 | (EP) . |
| WO93/00095 | 2/1993 | (WO) . |
| WO94/11360 | 5/1994 | (WO) . |
| WO95/18619 | 7/1995 | (WO) . |

OTHER PUBLICATIONS

Finkelstein et al., J. Org. Chem., 51(18), pp. 3548–3551 (1986).

Chemical Abstracts, vol. 122, No. 11, Abstract No. XP002032819 (Mar. 13, 1995).

Muathen, J. Chem. Res. Synop., No. 11, p. 405 (1994).

Ziegler et al., Journal of Organic Chemistry, 43(15), pp. 2941–2946 (1978).

Cortese et al., Journal of Organic Chemistry, 43(15), pp. 2952–2958 (1978).

Valentine et al., Journal of Organic Chemistry, 46, pp. 4614–4617 (1981).

Kraus et al., Tet. Lett., 35, pp. 9189–9190 (1994).

Heck et al., Journal of Organic Chemistry, 39, pp. 3327–3331 (1974).

Mori et al., Heterocycles, 16, pp. 1491–1498 (1981).

Perry, Chemtech, Feb., pp. 18–23 (1994).

* cited by examiner

Primary Examiner—Bruck Kifle
(74) Attorney, Agent, or Firm—William T. Han; William T. King; Charles M. Kinzig

(57) ABSTRACT

A new process for preparing substituted 7-aminocarbonyl-3-oxo-2,3,4,5-tetrahydro-1H-1,4-benzodiazepines is disclosed.

22 Claims, No Drawings

PROCESS FOR THE AMINOCARBONYLATION OF BENZAZEPINES AND BENZODIAZEPINES

This is a 371 of International Application PCT/IB96/01502, filed Dec. 27, 1996, which claims benefit from U.S. Provisional Application 60/009,531, filed Dec. 29, 1995.

FIELD OF THE INVENTION

This invention relates to processes and intermediates for preparing pharmaceutically active compounds. More, particularly, this invention relate to the aminocarbonylation of benzazepines and benzodiazepines.

BACKGROUND OF THE INVENTION

Tetraydro-1-benzazepines and tetrahydro-1,4-benzodiazepines form the core structure of a variety of pharmaceutically useful compounds. In particular, WO 93/00095 (PCT/US92/05463) and WO 94/14776 (PCT/US93/12436) disclose 7-aminocarbonyl tetrahydro-1-benzazepines and tetrahydro-1,4-benzodiazepines which are reported, to be inhibitors of the fibrinogen and vitronectin receptors and useful as inhibitors of platelet aggregation, osteoporosis, angiogenesis and cancer metastasis.

Methods to prepare such compounds typically employ a trisubstituted phenyl derivative as a starting material. The trisubstituted phenyl derivative incorporates two substituents to form the azepine ring, and a third substituent to introduce the 7-carbonyl substituent. Such starting materials may be difficult and costly to obtain, and may limit the chemistry which may be employed to form the azepine ring,. Prior processes generally introduce the aminocarbonyl group into the molecule via a 7-carboxyl group which is coupled to an amino group by conventional methods for forming amide bonds. Methods disclosed in WO 93/00095 and WO 94/14776 are exemplary.

We have now discovered new useful intermediates and a new process for preparing certain substituted 7-aminocarbonyl benzazepines and benzodiazepines. The new process uses a simple disubstituted benzene as a starting material, and also introduces the aminocarbonyl function in a single palladium catalyzed aminocarbonylation step. This process is more efficient than prior processes for preparing such compounds and adaptable to large scale synthesis.

Various types of palladium catalyzed reactions with aryl and vinyl halides are known to the art, and the problems attendant to their use with electron rich systems have been studied. For instance, Ziegler et al., *J. Org. Chem.* 1978, 43, 2941, report that highly activated aryl bromides, such as bromo-anilines, reacted very poorly in palladium catalyzed vinylic substitution reactions, but observed that some improvement was noted when aryl iodides were used, and when the palladium ligand was an tri-o-tolyl phosphine rather than a triphenylphosphine. Cortese et al., *J. Org. Chem.* 1978 43, 2952, report a palladium catalyzed vinylic substitution reaction on an o-iodo aniline.

Valentine et al., *J. Org. Chem.* 1981, 4614, suggest that the unreactivity of o-bromo-anilines toward carbonylation may be overcome by acetylation of the anilino amine group. Kraus et al., *Tet. Lett.* 1994 49, 9189 disclose an alkoxycarbonylation of a 7-triflic-tetrahydro-1,4benzodiazpine.

Heck et al., *J. Org. Chem.* 1974, 39, 3327, report typical conditions for aminocarbonylation reactions on aromatic systems; however, they do not report conditions for aminocarbonylation of electron-rich systems such as halo-anilines. Certain o-bromoanilines have been reported to undergo aminocarbonylation in low yield by Mori et al., *Heterocycles* 1981, 16 1491, and Perry, *Chemtech* Feb. 18, 1994 reports the use of iodo-aryl and amino-aryl monomers in a palladium catalyzed carbonylation reaction to prepare aramide polymers.

SUMMARY OF THE INVENTION

It is an object of is invention to provide a new and efficient process for the preparation of 7-aminocarbontyl benzazepines and benzodiazepines of formula (I):

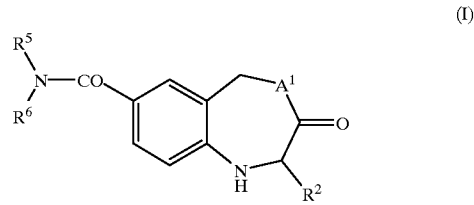

(I)

as hereinafter defined.

One aspect of this invention is an intermediate compound of formula (II):

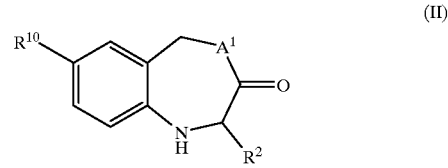

(II)

as hereinafter defined, wherein $R^{10}$ is Br or I.

Another aspect of this invention are processes for preparing a compound of formula (II), wherein $R^{10}$ is I or Br, from a compound of formula (IV):

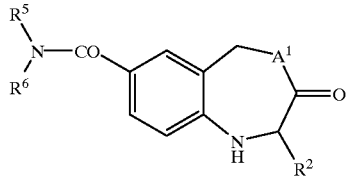

(IV)

wherein $R^2$ and $A^1$ are as defined for formula (I).

DETAILED DESCRIPTION

This invention comprises a process for preparing compounds of formula (I):

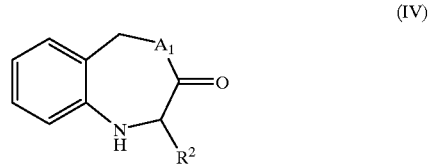

wherein
  $A^1$ is $NR^1$ or $CHR^1$;
  $R^1$ is H, T—$C_{1-6}$alyl, T—$C_{1-6}$oxoalkyl, T—$C_{2-6}$alkenyl, T—$C_{3-4}$oxoalkenyl, T—$C_{3-4}$oxoalkynyl, T—$C_{3-4}$alkynyl, $C_{3-6}$cycloalkyl, Ar or Het, optionally substituted by one or more of halo, —OR', —CN, —NR'$_2$, —NO$_2$, —CF$_3$, —CO$_2$R', —CONR'$_2$, Ar—C$_{0-6}$alkyl or Het-C$_{0-6}$alkyl, wherein T is H, C$_{3-6}$cycloalkyl, Het or Ar.

R$^2$ is CH$_2$CO$_2$R$^3$;

R$^3$ is H, C$_{1-6}$alkyl, C$_{3-7}$cycloalkyl-C$_{0-4}$alkyl or Ar—C$_{0-4}$alkyl;

R$^5$ is W—(CR'$_2$)$_q$—Z—(CHR')$^m$, and

R$^6$ is H, C$_{1-6}$alkyl, Ar—C$_{0-6}$alkyl, Het-C$_{0-6}$alkyl, or C$_{3-6}$cycloalkyl-C$_{0-6}$alkyl, or R$^5$ and R$^6$ together form a five- or six-membered Het ring which is substituted by W;

W is R$^9$R"N—, R'R"NR'N—, R'R"NR'NCO—, R'$_2$NR'NC(=NR')—, R'ONR'C(=NR')—,

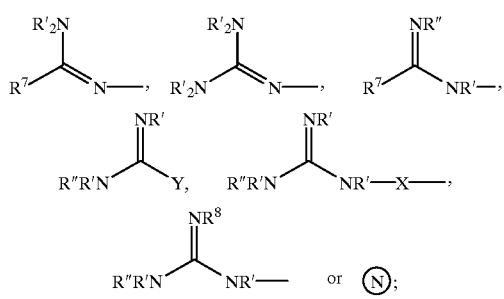

R' is H, C$_{1-6}$alkyl, C$_{3-7}$cycloalkyl-C$_{0-4}$alkyl or Ar—C$_{0-4}$alkyl;

R" is R', —C(O)R' or —C(O)OR'";

R'" is H, C$_{1-6}$alkyl or Ar—C$_{0-4}$alkyl;

R$^7$ is R', —CF$_3$, —SR', or —OR';

R$^8$ is R', C(O)R', CN, NO$_2$, SO$_2$R' or C(O)OR$^{15}$;

R$^9$ is H, C$_{1-6}$alkyl, C$_{3-7}$cycloalkyl-C$_{0-4}$alkyl, Het-C$_{0-4}$alkl or Ar—C$_{0-4}$alkyl;

X is N=CR', C(O) or O;

Y is absent, S or O;

Z is (CH$_2$)$_t$, Het, Ar or C$_{3-7}$cycloalkyl;

q is 0 to 3;

m is 0 to 2; and t is 0 to 2;

which process comprises:

reacting a compound of formula (II):

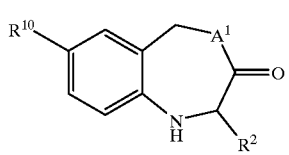

wherein

A$^1$ and R$^2$ are as defined above for formula (I); and

R$^{10}$ is Cl, Br, I, FSO$_3$—, ClSO$_3$— or CF$_3$SO$_3$—;

with a Pd catalyst, carbon monoxide and an amine of the formula (III)

wherein R$^5$ and R$^6$ are defined as above in formula (I) except that any basic nitrogen group in R$^5$ or R$^6$ is protected, and thereafter removing any protecting groups.

Suitably R$^1$ is H, C$_{1-6}$alkyl or Ar—C$_{1-4}$alkyl. Preferably R$^1$ is H. methyl, ethyl, i-propyl, benzyl or phenylethyl. Most preferably R$^1$ is methyl.

Suitably R$^3$ is C$_{1-6}$alkyl, Ar or Ar—C$_{1-4}$alkyl. Preferably R$^3$ is methyl, t-butyl or benzyl.

Preferably, R$^{10}$ is Br or I.

Typically the process is carried out by combining the compound of formula (II) with the palladium catalyst, the amine of formula (III) and a base in a suitable solvent and heating the reactants under an Atmosphere of carbon monoxide.

Any stable palladium(0) or palladium(II) source is a suitable catalyst for the aminocarbonylation. (Ph$_3$P)$_4$Pd, bis(dibenzylideneacetone)Pd(0), bis(di-(1,2-diphenylphosphino)ethane)Pd(O), PdCl$_2$, Pd(OAc)$_2$, (Ph$_3$P)$_2$PdCl$_2$ or (Ph$_3$P)$_2$Pd(OAc)$_2$ are typical.

However, tetrahydro-benzazepine/benzodiazepines in which a bromide is para to an azepine —NH— are electron rich and, like p-bromo anilines, react poorly in aminocarbonylation reactions under the normal conditions reported for such reactions. It has now been discovered that catalyst loading and the addition of a suitable ligand for the palladium are important parameters in such reactions. For instance, at a catalyst loading of about 20 mole % of (Ph$_3$P)$_4$Pd and 25 mole % of triphenyl phosphine, the aminocarbonylation reaction is complete after 5–6 h; whereas, at a catalyst loading of 5 mole % the reaction does not proceed at all. A loading of about 15–100 mole % is suitable, typically about 20–25 mole % produces optimal results. Triphenyl phosphine is a preferred ligand for use in the reaction, as it stabilizes and solubilizes the palladium(0) and provides an active complex. Other ligands may be used, but they generally provide either too much stabilization so that the complex is inert, or do not provide enough stabilization so that the metal precipitates.

In spite of the advances realized by the combined use of high catalyst loadings and added Pd ligand, the cost of the palladium required for the high loading is a serious drawback to the use of such conditions for an industrial process. Thus, in another aspect, this invention is also an improvement which comprises conducting the reaction in the presence of a small amount of a reducing agent. Thus, if the reaction is run in the presence of a suitable reducing agent, such as ammonium formate, cyclohexadiene. hydroquinone, sodium iodide, sodium borohydride or hydrazine hydrate much lower catalyst loadings may be used. Typically, the amount of reducing agent is greater than about 15 mole %, with about 20–25 mole % being especially suitable. The reducing agent is believed to facilitate the conversion of the palladium present in the reaction to Pd(0). Thus, with the addition of added reducing agent and added triphenyl phosphine, catalyst loadings in the range of about 0.5–5% are typical, with about 2% being fairly suitable. These conditions also permit the use of much cheaper sources of palladium in the reaction, such as (Ph$_3$P)$_2$Pd(OAc)$_2$ and (Ph$_3$P)$_2$Pd(Cl)$_2$. Pd(OAc)$_2$ is a preferred catalyst.

It has been further found that the use of an iodide as the activated aryl species greatly facilitates the aminocarbonylation reaction. Thus, when the iodide is used. neither an added palladium ligand, nor a reducing agent, nor excessive catalyst loading is required to achieve acceptable results. (Ph₃P)₂Pd(Cl)₂ is a preferred catalyst for the aryl iodide.

The reaction may be run in any solvent which is unreactive with the reactants, but a solvent which is able to solvate the palladium species is preferred. Toluene, DMF, acetonitrile and dimethylacetamide are suitable, but N-methylpyrrolidinone is preferred.

Suitably, the temperature of the aminocarbonylation reaction is about 70–130° C. Preferably the reaction is run around 90–115° C., more preferably around 100° C.

The aminocarbonylation reaction may be run without high pressures of carbon monoxide. About one atomsphere is typical and preferred. Carbon monoxide may also be bubbled through the reaction mixture to saturate the solution.

Typically a base will be included in the reaction mixture to liberate the amine component (III) if it is used as a salt. In addition, the base may be used to consume the acid H—$R^{10}$ which may be produced during the reaction. Tertiary amines are most suitable for this purpose, such at tributylamine, tetramethylethylenediamine and Hunigs base. Hunigs base, diisopropylethylamine, is especially suitable.

The amine component (III) is generally a basic primary or secondary amine, wherein any other reactive basic centers are protected by an amino protecting group. Protecting groups for such reactive centers, and methods to remove such protecting groups, are well known in the art and are disclosed for instance by Greene et al., PROTECIVE GROUPS IN ORGANIC SYNTHESIS, Second Edition, John Wiley & Sons, New York, 1991. Optionally substituted benzyloxycarbonyl, alkyloxycarbonyl, acetyl or benzoyl groups are exemplary. Amino, guanidino and amidino groups are examples of other reactive centers in the amine component which would be protected. The butyloxycarbonyl and benzyloxycarbonyl groups are preferred protecting groups. It will be appreciated, however, that when a symmetric amino component, such as 4,4'-bipiperidine, is used, it may be unnecessary to protect the second basic center. The protecting groups are subsequently removed by methods well known in the art, such as by treatment with acid, for instance trifluoroacetic acid or hydrochloric acid, or by hydrogenation over a palladium or platinum catalyst.

Representative amines of formula (III) are:

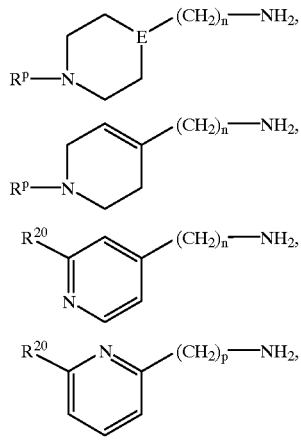

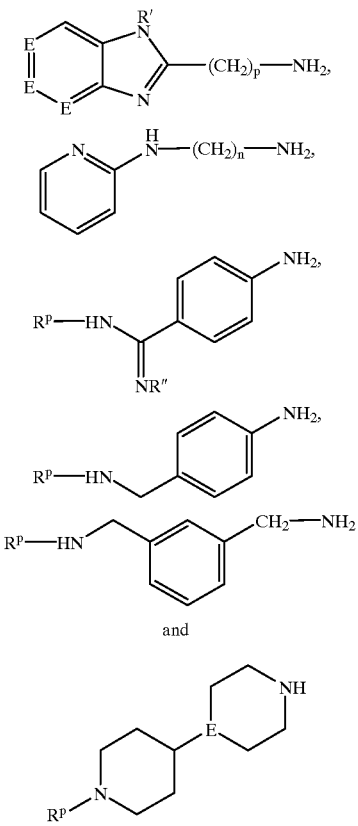

wherein E is N or CR', $R^p$ is H or an amino protecting group, such as benzyloxycarbonyl, t-butyloxycarbonyl or acetyl, n and p are 0–3, and $R^{20}$ is hydrogen, amino, mono or di-$C_{1-4}$alkylamino, hydroxy or $C_{1-4}$alkyl. Preferably n is 2 and p is 1. N'-Benzyloxy-4,4'-bipiperidine and N'-t-butyloxycarbonyl-4,4'-bipiperidine are especially suitable amines.

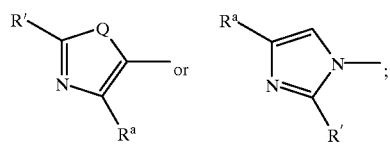

In a particular embodiment W is or $R^a$ is H, $C_{1-6}$alkyl, Ar—$C_{0-6}$alkyl, Het-$C_{0-6}$alkyl, or $C_{3-6}$cycloalkyl-$C_{0-6}$alkyl, halogen, $C_{1-6}$alkyl, $OR^1$, $SR^1$, $COR^1$, OH, $NO_2$, $N(R^1)_2$, $CO(NR^1)_2$, $CH_2N(R^1)_2$;

$R^b$ and $R^c$ are independently selected from H, $C_{1-6}$alkyl, Ar—$C_{0-6}$alkyl, Het-$C_{0-6}$alkyl, or $C_{3-6}$cycloalkyl-$C_{0-6}$ alkyl, halogen, $C_{1-6}$alkyl, $OR^1$, $SR^1$, $COR^1$, OH, $NO_2$, $N(R^1)_2$, $CO(NR^1)_2$, $CH_2N(R^1)_2$, or $R_b$ and $R_c$ are joined together to form a five or six membered aromatic or non-aromatic ring, optionally substituted by halogen, $C_{1-4}$alkyl, $OR^1$, $SR^1$, $COR^1$, OH, $NO_2$, $N(R^1)_2$, $CO(NR^1)_2$, $CH_2N(R^1)_2$;

Q is NR', O or S;

R' is H, $C_{1-6}$alkyl, $C_{3-7}$cycloalkyl-$C_{0-4}$alkyl or Ar—$C_{0-4}$alkyl.

In another particular embodiment, W is a six-membered nitrogen heterocycle, such as piperidinyl.

In a specific embodiment, this invention is a method for preparing 7-bipiperidin-1-yl]carbonyl]-3-oxo-2,3,4,5- tetrahydro-1H-1,4-benzodiazepine acetic acid, comprising reacting 7-iodo-3-oxo-2,3,4,5-tetrahydro-1H-1,4-benzodiazepine acetic acid, or an ester thereof, with an optionally 1'-protected 4-4'-bipiperidine, carbon monoxide and a palladium catalyst, and thereafter removing any protecting groups.

It will also be appreciated that the process of this invention may be used to aminocarbonylate an anilino precursor of the tetrahydro-1-benzazepine and tetrahydro-1,4-benzodiazepines of this invention prior to formation of the azepine ring.

The reactive tetrahydro-1-benzazepine or tetrahydro-1,4-benzodiazepine intermediate (II) which is used in the aminocarbonylation reaction may be prepared by methods analogous to those described in WO 94/14776 starting with a suitably trisubstituted halo-phenyl or hydroxy-phenyl compound. The carboxyl function of such intermediates is usually in protected form. Esters are typical protecting groups for the carboxyl function of the compounds of formula (II), especially methyl, ethyl, cyclohexyl, phenyl and benzyl esters. These are may be removed by conventional procedures, such as by hydrolysis with a base, for instance an alkali hydroxide or carbonate, or by hydrogenation over a palladium or platinum catalyst.

In yet another aspect, this invention is a process for preparing the intermediate compound of formula (II), as defined above, wherein $R^{10}$ is Br, which comprises reacting a compound of formula (IV):

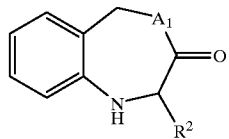

(IV)

wherein $A^1$, $A^2$ and $R^2$ are as defined in formula (I), with N-bromosuccinimide and a tetraakyl ammonium halide. Tetrabutylammonium bromide is especially suitable. Although the mechanism is not known, the use of the tetraalkyl ammonium halide promotes bromination para to the anilino nitrogen with a reduced amount of the di-halogenated product. This process is more economical than bromination with tetrabutyl ammonium tribromide, which is a costly reagent, and it also avoids the di-halogenation realized when NBS is used alone. 7,9-Dibromination occurs at about 15% when NBS is used alone; whereas, use of the tetrabutylammonium bromide reduces the production of this by product to less than 1%.

In accordance with the above process, a useful intermediate compound of this invention is given by formula (IV):

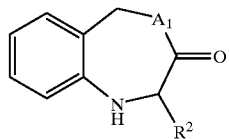

(IV)

wherein $A^1$, $A^2$ and $R^2$ are as defined in formula (I).

In another aspect, this invention is method for preparing the intermediate compound of formula (II), as defined above, wherein $R^{10}$ is I, which comprises reacting a compound of formula (IV):

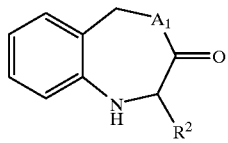

(IV)

wherein $A^1$ and $R^2$ are as defined in formula (I), with the ICl.pyridine complex. Iodination of tetrahydro-1-benzazepines and tetrahydro-1,4benzodiazepines is difficult to accomplish because the nitrogen in the 1-position tends to undergo oxidation under the conditions necessary for iodination giving a double bond at C2 in the azepine ring. It has been discovered that a suitable reagent for accomplishing this transformation is the ICl.pyridine complex. In fact, this reagent is the only source of $I^+$ that does not produce appreciable oxidation of the tetrahydro-1-benzazepine/ tetrahydro-1,4-benzodiazepine to yield the corresponding dihydro azepine/diazepine.

In a preferred embodiment, the iodination reaction is carried out in a methanol/methylene dichloride or a water/ methylene chloride solvent mixture. Using this co-solvent mixture conversions on the order of 95% are realized, whereas, if the reaction is conducted using only methylene dichloride as the solvent the reaction stops at 75–80% conversion.

The meaning of any substituent at any one occurrence in formulas (I)–(IV) or any subformula thereof is independent of its meaning, or any other substituent's meaning, at any other occurrence, unless specified otherwise.

Abbreviations and symbols commonly used in the chemical arts are used herein to describe the compounds, reactions and reagents of this invention. All "loadings" expressed herein, such as catalyst loading, are expressed as a mole % of the aromatic halide or triflate.

$C_{1-4}$alkyl as applied herein is meant to include methyl, ethyl, n-propyl, isopropyl, n-butyl isobutyl and t-butyl. $C_{1-6}$alkyl additionally includes pentyl, n-pentyl, isopentyl, neopentyl and hexyl and the simple aliphatic isomers thereof. Any $C_{1-4}$alkyl or $C_{1-6}$alkyl group may be optionally substituted by halo, —OR, SR', —CN, —NR'R', —NO$_2$, —CF$_3$, CF$_3$S(O)$_r$—, CO$_{R'}$, —CONR'$_2$, $C_{3-6}$cycloalkyl, Het or Ar, unless otherwise indicated. $C_{0-4}$alkl and $C_{0-6}$alkyl additionally indicates that no alkyl group need be present (e.g., that a covalent bond is present).

$C_{2-6}$ alkenyl as applied herein means an alkyl group of 2 to 6 carbons wherein a carboncarbon single bond is replaced by a carbon-carbon double bond. $C_{2-6}$alkenyl includes ethylene, 1-propene, 2-propene, 1-butene, 2-butene, isobutene and the several isomeric pentenes and hexenes. Both cis and trans isomers are included. Any sp$^3$ carbon atom in the $C_{2-6}$alkenyl group may be optionally substituted by halo, —OR', SR', —CN, —NR'R', —NO$_2$, —CF$_3$, CF$_3$S (O)$_r$—, —CO$_2$R', —CONR'$_2$, $C_{3-6}$cycloalkyl, Het or Ar.

$C_{3-6}$ alkynyl means an alkyl group of 3 to 6 carbons wherein one carbon-carbon single bond is replaced by a carbon-carbon triple bond. $C_{3-6}$ alkynyl includes acetylene, 1-propyne, 2-propyne, 1-butyne, 2-butyne, 3-butyne and the simple isomers of pentyne and hexyne. Any sp$^3$ carbon atom in the $C_{3-6}$alkynyl group may be optionally substituted by halo, —OR', SR', —CN, —NR'R', —NO$_2$, —CF$_3$, CF$_3$S(O)$_r$—, —CO$_2$R', —CONR'$_2$, $C_{3-6}$cycloalkyl, Het or Ar.

$C_{1-4}$oxoalkyl refers to an alkyl group of up to four carbons wherein a CH$_2$ group is replaced by a C(O), or carbonyl, group. Substituted formyl, acetyl, 1-propanal, 2-propanone, 3-propanal, 2-butanone, 3-butanone, 1- and 4-butanal groups are representative. $C_{1-6}$oxoalkyl includes additionally the higher analogues and isomers of five and six carbons substituted by a carbonyl group. $C_{3-6}$oxoalkenyl and $C_{3-6}$oxoalkynyl refers to a $C_{3-6}$alkenyl or $C_{3-6}$alkynyl group wherein a $CH_2$ group is replaced by $C(O)$ group. $C_{3-4}$oxoalkenyl includes 1-oxo-2-propenyl, 3-oxo-1-propenyl, 2-oxo-3-butenyl and the like.

A substituent on a $C_{1-6}$ alkyl, $C_{2-6}$ alkenyl, $C_{2-6}$ alkynyl or $C_{1-6}$ oxoalkyl group, may be on any carbon atom which results in a stable structure, and is available by conventional synthetic techniques.

T—$C_{1-6}$ alkyl refers to a $C_{1-6}$ alkyl group wherein in any position a carbon-hydrogen bond is replaced by a carbon-T bond. T—$C_{2-6}$ alkenyl and T—$C_{3-6}$ alkynyl have a similar meaning with respect to $C_{2-6}$ alkenyl and $C_{3-6}$ alkynyl.

Ar, or aryl, as applied herein, means phenyl or naphthyl, or phenyl or naphthyl substituted by one to three moieties. In particular, such moieties may be $C_{1-4}$alkyl, $C_{1-4}$alkoxy, $C_{1-4}$alkylthio, trifluoromethyl, OH, F, Cl, Br or I.

Het, or heterocycle, indicates an optionally substituted five or six membered monocyclic ring, or a nine or ten-membered bicyclic ring containing one to three heteroatoms chosen from the group of nitrogen, oxygen and sulfur, which are stable and available by conventional chemical synthesis. Illustrative heterocycles are benzofuran, benzimidazole, benzopyran, benzothiophene, furan, imidazole, indoline, morpholine, piperidine, piperazine, pyrrole, pyrrolidine, tetrahydropyridine, pyridine, thiazole, thiophene, quinoline, isoquinoline, and tetra- and perhydro-quinoline and isoquinoline. A six membered ring heterocycle containing one or two nitrogens, such as piperidine, piperazine, tetrahydropyridine and pyridine, are preferred heterocycles. Piperidine is a preferred Het for the moiety Z.

$C_{3-7}$cycloalkyl refers to an optionally substituted carbocyclic system of three to seven carbon atoms, which may contain up to two unsaturated carbon-carbon bonds. Typical of $C_{3-7}$cycloalkyl are cyclopropyl, cyclobutyl, cyclopentyl, cyclopentenyl, cyclohexyl, cyclohexenyl and cycloheptyl. Any combination of up to three substituents, such as chosen from $C_{1-4}$alkyl, $C_{1-4}$alkoxy, $C_{1-4}$alkylthio, trifluoromethyl, OH, F, Cl, Br or I, on the cycloalkyl ring that is available by conventional chemical synthesis and is stable, is within the scope of this invention.

Ⓝ as used herein indicates a nitrogen heterocycle, which may be a saturated. or unsaturated stable five-, six- or seven-membered monocyclic ring, or a seven- to ten-membered bicyclic ring containing up to three nitrogen atoms or containing one nitrogen atom and a heteroatom chosen from oxygen and sulfur, and which may be substituted on any atom that results in a stable structure. The nitrogen atom in such ring may be substituted so as to result in a quaternary nitrogen. The nitrogen heterocycle may be substituted in any stable position by $R^{20}$, for instance H, $C_{1-4}$alkoxy, F, Cl, Br, I, $NO_2$, $NR'_2$, OH, $CO_2R'$, $CONHR'$, $CF_3$, T—$C_{0-4}$alkyl, T—$C_{1-4}$alkyl-$S(O)_u$ (e.g., where u is 0, 1 or 2) or $C_{1-4}$alkyl substituted by any of the aforementioned sustituents. Representative of Ⓝ are pyrroline, pyrrolidine, imidazole, benzimidazole, aza-benzimidazole, imidazoline, imidazolidine, pyrazole, pyrazoline, pyrazolidine, piperidine, piperazine, morpholine, pyridine, pyridinium, tetrahydropyridine, tetrahydro- and hexahydro-azepine, quinuclidine, quinuclidinium, quinoline, isoquinoline, and tetra- and perhydro-quinoline and isoquinoline. In particular, Ⓝ may be pyridyl, pyrolidinyl, piperidinyl, piperazinyl, azetidinyl, quinuclidinyl or tetrahydropyridinyl. Ⓝ is preferably 2 or 4-pyridyl, 2-(6-amino-pyridyl), 4-(2-amino-pyridyl), 4-tetrahydropyridyl, 4-piperidinyl or 4-piperazinyl.

When Ⓝ is a heterocycle of the formula

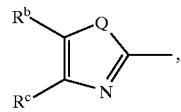

$R^b$ and $R^c$ are joined together to form a five- or six-membered aromatic or non-aromatic ring. The ring formed will generally be a five- or six-membered heterocycle selected from those listed above for Het, or will be a phenyl, cyclohexyl or cyclopentyl ring. Phenyl, 2,3-pyridyl (e.g., where the five-membered ring is formed between the 2 and 3 positions of a pylidyl ring), 3,4-pyridyl, 4,5 pyridyl and 4,5-pyrimidyl, each optionally substituted by $C_{1-4}$alkyl are preferred moieties for such a ring.

Certain radical groups are abbreviated herein. t-Bu refers to the tertiary butyl radical, Boc refers to the t-butyloxycarbonyl radical, Fmoc refers to the fluorenyl-methoxycarbonyl radical, Ph refers to the phenyl radical, Cbz refers to the benzyloxycarbonyl radical, Bn refers to the benzyl radical, Me refers to methyl, Et refers to ethyl, Ac refers to acetyl, Alk refers to $C_{1-4}$alkyl, Nph refers to 1- or 2-naphthyl and cHex refers to cyclohexyl.

Certain reagents are abbreviated herein. DCC refers to dicyclohexylcarbodiimide, DMAP refers to dimethylaminopyridine, DIEA refers to diisopropyletlylunine, THF refers to tetrahydrofuran, DMF refers to dimethyl formamide, NBS refers to N-bromosuccinimide, Pd/C refers to a palladium on carbon catalyst, TEA refers to triethylamine, TFA refers to trifluoroacetic acid.

If the amine component of the amide bond-forming reaction contains a protecting group, the protecting group can be removed either prior or subsequent to the ester hydrolysis step, using methods suitable for selective deprotection of the specific protecting group employed. Such methods are described in Green, "Protective Groups in Organic Synthesis" (published by Wiley-Interscience). For example, if the amine component contains a nitrogen group which is protected by a tert-butoxycarbonyl (BOC) group, the BOC group is removed under acidic conditions, using, for instance, HCl in dioxane or trifluoroacetic acid (TFA) in $CH_2Cl_2$.

The simple starting materials for preparing the compounds of this invention are commercially available or prepared by routine methods well known in the art.

The intermediate compounds of this invention are useful as intermediates in the preparation of pharmaceutically active compounds, in particular compounds which have fibrinogen and vitronectin antagonist properties.

General

Nuclear magnetic resonance spectra were recorded at either 250 or 400 MHz using, respectively, a Bruker AM 250 or Bruker AC 400 spectrometer. $CDCl_3$ is deuteriochloroform, $DMSO-d_6$ is hexadeuteriodimethylsulfoxide, and $CD_3OD$ is tetradeuteriomethanol. Chemical shifts are reported in parm per million (δ) downfield from the internal standard tetramethylsilane. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. Continuous wave infrared (IR) spectra were recorded on a Perkin-Elmer 683 infrared spectrometer, and Fourier trans-form infrared (FTIR spectra were recorded on a Nicolet Impact 400 D infrared spectrometer. IR and FIIR spectra were recorded in transmission mode, and band positions are reported in inverse wavenumbers ($cm^{-1}$). Mass spectra were taken on either VG 70 FE, PE Syx API III, or VG ZAB HF instruments, using fast atom bombardment (FAB) or electrospray (ES) ionization techniques. Elemental analyses were obtained using a Perkin-Elmer 240C elemental analyzer. Melting points were taken on a Thomas-Hoover melting point apparatus and are uncorrected. All temperatures are reported in degrees Celsius.

Analtach Silica Gel GF and E. Merck Silica Gel 60 F-254 thin layer plates were used for thin layer chromatography. Both flash and gravity chromatography were carried out on E. Merck Kieselgel 60 (230–400 mesh) silica gel. Analytical and preparative HPLC were carried out on Raini or Beckman chromatographs. ODS refers to an octadecylsilyl derivatized silica gel chromatographic support. 5$\mu$ Apex-ODS indicates an octadecylsilyl derivatized silica gel chromatographic support having a nominal particle size of 5$\mu$, made by Jones Chromatography, Littleton, Colo. YMC ODS-AQ® is an ODS chromatographic support and is a registered trademark of YMC Co. Ltd., Kyoto, Japan. PRP-1® is a polymeric (styrene-divinylbenzene) chromatographic support, and is a registered trademark of Hamilton Co., Reno, Nev. Celite® is a filter aid composed of acid-washed diatomaceoug silica, and is a registered trademark of Manville Corp., Denver, Colo.

The following procedures illustrate the method of carrying out the invention.

Preparation of the Tetrahydro-3-oxo-1,4-benzodiazepine Ring System

EXAMPLE 1

Preparation of Methyl (S)-2,3,4,5-tetrahydro-3-oxo-1H-1,4-benzodiazepine-2-acetate a) Dimethyl (R)-malate O-triflate A solution of dimethyl (R)-malate (12.96 g, 80 mmol) and pyridine (6.8 mL, 84 mmol) in $CH_2Cl_2$ (50 mL) was added dropwise under argon at 0° to a solution of triflic anhydride (14.2 mL, 84 mmol) in dry $CH_2Cl_2$ (40 mL) in a flame-dried flask. The resulting yellow-orange mixture was stirred at 0° C. for 30 min, and then at RT for 4 h. The reaction was quenched by adding $H_2O$ (50 mL) and the organic phase was washed three times with $H_2O$ and brine, dried ($MgSO_4$), and concentrated to give the title compound as an off white solid (22.45 g, 95%): MS (ES) m/e 295.0 [M+H]$^+$.

b) Dimethyl N-[2-(cyano)phenyl]-(S)-aspartate

A solution of compound of Example 1(a) (22.4 g, 76.2 mmol) in 1:1 $CH_3Cl$:hexane (80 mL) was added to a solution of 2-aminobenzonitrile (9.0 g, 76.2 mmol) and 2,6-di-tert-butylpyridine (14.5 g, 76.2 mmol) in 1:1 $CH_3Cl$-hexane (100 mL) in a flame-dried flask under argon at 0° C. The resulting mixture was stirred at 0° C. for 30 min and then at RT for 3 d. The resulting mixture was concentrated, the residue was taken up into EtOAc, washed with 5% HCl and brine, and dried ($MgSO_4$). The resulting mixture was concentrated and the residue was purified by flash chromatography (silica gel, 12% EtOAc/hexane) to give the title compound as a clear oil (12.3g, 62%): MS (ES) m/e 263.3 [M+H]$^+$.

c) Methyl (S)-2,3,4,5-Tetrahydro-3-oxo-1H-1,4-benzodiazepine-2-acetate

A mixture of compound of Example 1(b)(12 g, 45.7 mmol), $Et_3N$ (7.64 mL, 54.84 mmol), and Raney-Ni (46 g, prewashed by $CH_3OH$) in $CH_3OH$ (200 mL) was stirred at RT under a $H_2$ balloon for 2 d. The mixture was filtered and the catalyst was washed 3× with $CH_3OH$. The filtrate was concentrated and the residue was purified by flash chromatography (silica gel step gradient, 0–5% $CH_3OH/CH_2Cl_2$) to yield the title compound as a white solid (7.93 g, 74%): MS (ES) m/e 235.3 [M+H]$^+$. The title compound was shown to contain approximately 23% of the (R)-enantiomer by NMR.

Bromination of the tetrahydro-3-oxo-1,4-benzodiazepine

EXAMPLE 2

Preparation of Methyl 2,3,4,5-tetrahydro-7-bromo-4-methyl-3-oxo-1H-1,4-benzodiazepine-2-acetate Methyl 2,3,4,5-tetrahydro-4-methyl-3-oxo-1H-1,4-benzodiazepine-2-acetate (100 g, 0.4 mole) and n-$Bu_4$N Br (13 g, 0.04 mole) were added to $CH_2Cl_2$ (1.0 liter) and refluxed for 0.5 hr. The reaction mixture was cooled to 28° C. and N-Bromosuccinimide added in small portions (72.8 g, 0.41 mole). The reaction was stirred at ambient temperature for 1.0 hr then washed with 5% $NaHCO_3$ solution (400 ml) then water (2×400 ml) $CH_2Cl_2$ (800 ml) was replaced with hexane (800 ml) via 'put and take' distillation, the resulting slurry was cooled, filtered and washed with hexane. The product was dried in vacuo to yield the title compound (123 g, 93%). HPLC analysis showed 0.7% residual starting material and 0.7% 7,9-dibromide.

Iodination of the tetrahydro-3-oxo-1,4-benzodiazepine

EXAMPLE 3

Preparation of Methyl (S)-2,3,4,5-tetrahydro-7-iodo-3-oxo-1H-1,4-benzodiazepine-2-acetate Pyridine-ICl complex: 1M iodinemonochloride in $CH_2Cl_2$ (100 mL) was added slowly to a solution of pyridine (8.5 mL, 105 mmol) in $CH_2Cl_2$ (20 mL), stirred under argon and pre-cooled to 50° C., so as to maintain an internal temperature between 10–15° C. The mixture was stirred at 5–10° C. for 20 min. Hexane (50 mL) was added and the mixture was stirred in a cold bath for an additional 30 min. The solid which formed was collected by filtration, washed with hexane and with petroleum ether, and dried to yield pyridine-ICl complex (22.5 g) as a yellow solid which was used without further purification.

Pyridine-ICl complex (1.27 g, 5.28 mmol) was added portionwise to a solution of the methyl (S)-2,3,4,5-tetrahydro-1-oxo-1H-1,4-benzodinapine-2-acetate (1.18 g, 4.8 mmol) in 1:1 $CH_2Cl_2$: $CH_3OH$ (40 mL). The resulting mixture was stirred at RT for 40 min, treated with 1M $NaHSO_3$ (20 mL), and the resulting solid was collected by filtration, washed with $Et_2O$, and dried to yield the title compound as an off white solid (1.72 g, quantitative): MS (ES) m/e 361.2 [M+H]$^+$.

EXAMPLE 4

Preparation of Methyl 2,3,4,5-tetrahydro-7-iodo-4-methyl-3-oxo-1H-1,4-benzodiazepine-2-acetate Methyl 2,3,4,5-tetrahydro-3-oxo-4-methyl-1H-1,4-benzodiazepine-2-acetate (80 g, 0.32 mole) was added to $CH_2Cl_2$ (400 ml) and MeOH (400 ml). The mixture was heated at 40° C. for 0.5 hr then cooled to 25° C. Pyridine iodine monochloride complex was added in portions (82g, 0.51 mole). After the addition, the reaction was stirred for 10 minutes then $CH_2Cl_2$ (400 ml) added. The reaction mixture was stirred for 1.0 hr then washed with sodium metabisulphite solution (5 g+400 ml water), followed by water (400 ml). The temperature was maintained at 30° C. during the washing process. CH₂Cl₂ (450 ml) was replaced with 60/80 petrol (450 ml by 'put and take' distillation. A further portion of CH₂Cl₂ (200 ml) was replaced with 60/80 petrol, the mixture cooled slowly to 10° C., and the product filtered off and washed with 60/80 petrol. The product was dried in vacuo to yield the title compound (108 g, 92%).

EXAMPLE 5

Preparation of Methyl 2,3,4,5-tetrahydro-7-iodo-4-methyl-3-oxo-1H-1,4-benzodiazepine-2-acetate Methyl 2,3,4,5-tetrahydro-4-methyl-3-oxo-1H-1,4-benzodiazepine-2-acetate (100 g, 0.4 moles) was added to CH₂Cl₂ (500 ml) plus MeOH (500 ml) and heated at 40° C. for 0.5 hr. The solution was cooled to 26° C. and pyridine (64 g, 0.8 mole) added. Iodine monochloride (71.3 g, 0.44 mole) dissolved in CH₂Cl₂ (500 ml) was added dropwise over 30 minutes and the reaction stirred for a further 1.0 hr. The product was filtered off, washed with 60/80 petrol and dried in vacuo to yield the title compound (113 g, 75%).
Aminocarbonylation of tetrahydro-3-oxo-1,4-benzodiazepines

EXAMPLE 6

Preparation of 2,3,4,5-Tetrahydro-7-[[(N'-benzyloxycarbonyl)-4,4'-bipiperidinyl]carbonyl]-4-methyl-3-oxo-1H-1,4-benzodiazepine-2-acetic acid a) methyl (R,S) 7-(4,4'-bipiperidin-1-yl)-2,3,4,5-tetrahydro-4-methyl-3-oxo-1H-1,4-benzodiazepine-2-acetate Methyl 2,3,4,5-tetrahydro-7-bromo-4-methyl-3-oxo-1H-1,4benzodiazepine-2-acetate (5 g, 0.015 mole), Hunigs base, (18.2 g, 0.14 mole), Ph₃P (0.31 g, 0.0031 mole), Pd(OAc)₂ (0.07 g,0.00031 mole) and N-Cbz-4,4'-bipiperidine-HCl salt (7.3 g, 0.021 mole) were dissolved in N-methylpyrrolidinone (40 ml). The reaction mixture was heated to 110° C. whilst bubbling carbon monoxide through the solution. The temperature was maintained at 110° C. keeping the reaction under 1 atmosphere of carbon monoxide. Ammonium formate solution (0.5 ml of 0.6 g in 5 ml water) was added each hour, total reaction time 4 hours (2.0 ml added).

Excess Hunigs base was the distilled off under vacuum and the residue cooled and diluted with CH₂Cl₂ (30 ml). This was washed with water (2×30 ml). Tne CH₂Cl₂ was removed under vacuum and the residue dissolved in EtOAc (80 ml). The solution was stirred for three days then filtered and washed with cold EtOAc (6.52 g, 74%).

b) methyl (R,S) 7-(4,4'-bipiperidin-1-yl)-2,3,4,5-tetrahydro-4-methyl-3-oxo-1H-1,4-benzodiazepine-2-acetate A solution of the compound of Example 6(a) (0.06 mmol) in methanol (25 mL) containing 1.0M hydrogen chloride in ether (0.6 mL) was treated with 10% palladium hydroxide and the mixture was shaken in a hydrogen atmosphere (40 psi) for 1 h. The mixture was filtered and concentrated to yield the title compound.

c) (R,S) 7-(4,4'-bipiperidin-1-yl)-2,3,4,5-tetrahydro-4-methyl-3-oxo-1H-1,4-benzodiazepine-2-acetic acid The compound of Example 6(b) (0.26 mmol) is dissolved in methanol (9 mL), and 1.0 N sodium hydroxide (0.81 mL, 0.81 mmol) was added. The solution was stirred at RT overnight, and concentrated. The residue was dissolved in water/acetonitrile (3 mL), cooled to 0° C., acidified with HCl, and concentrated to yield the title compound.

EXAMPLE 7

Preparation of (S)-2,3,4,5-Tetrahydro-7-[[[benzimidazol-2-yl)methyl]methylamino]carbonyl]-3-oxo-1H-1,4-benzodiazepine-2-acetic acid a) Methyl (S)-2,3,4,5-tetrahydro-7-[[N-[(benzimidazol-2-yl)methyl]-N-methylamino]carbonyl]-3-oxo-1H-1,4-benzodiazepine-2-acetate A mixture of methyl (S)-2,3,4,5-tetrahydro-7-bromo-3-oxo-1H-1,4-benzodiazepine-2-acetate (1.5 g, 4.77905 mmol), 2-(methylaminoinethyl)benzimidazole dihydrochloride (2.24 g, 9.5809 mmol), triphenylphosphine (1.26 g, 4.7905 mmol), n-Bu₃N (6.21 g, 33.5333 mmol), and (Ph₃P)₄Pd (1.10 g, 0.9581 mmol) in N-methyl 2-pyrrolidinone (20 mL) was flushed with argon and carbon monoxide for 10 min. The mixture was then heated at 100–105° C. under a carbon monoxide balloon for 8 hr. The mixture was cooled and acidified with 6 N HCl to pH=2. The solution was extracted with EtOAc, and the EtOAc layer was discarded. The aqueous layer was neutralized with 30% NaOH and extracted with CH₂Cl₂. The organic extracts were dried over MgSO₄, concentrated, and purified by silica gel flash column chromatography (5% MeOH/CH₂Cl₂) to give the title compound (1.62 g, 80%) as an off white solid: ¹H NMR (250 MHz, DMSO-d₆): δ2.65 (dd, J=16.3, 7.6 Hz, 1H), 2.81 (dd, J=16.3, 5.9 Hz, 1H), 3.05 (s, 3H), 3.60(s, 3H), 3.75 (dd, J=16.3, 6.9 Hz, 1H), 4.78 (s, 2H), 4.95 (m, 1H), 5.05 (dd, J=16, 5.3 Hz, 1H), 6.20 (d, J=5.9 Hz, 1H), 6.55 (d, J=7.6 Hz, 1H), 7.25 (m, 4H), 7.55 (m, 2H), 8.21 (t, J=5.3 Hz, 1H).

b) (S)-2,3,4,5-Tetrahydro-7-[[[benzimidazol-2-yl)methyl]methylamino carbonyl]-3-oxo-1H-1,4-benzodiazepine-2-acetic acid Following the procedure of Example 7(a), methyl (S)-2,3,4,5-tetrahydro-7-[[N-[(benzimidazol-2-yl)methyl]-N-methylamino]carbonyl]-3-oxo-1H-1,4-benzodiazepine-2-acetate was saponified to afford the title compound (0.060 g, 57%) as an off white solid: ¹H NMR (400 MHz, DMSO-d₆) δ2.52 (dd,J=16.3, 7.6 Hz, 1H), 2.84 (dd, J=16.3, 5.9 Hz, 1 Hz, 3.20 (s, 3H), 3.75 (dd, J=16.3, 6.9 Hz, 1H), 4.95 (t, J=5.9 Hz, 1H), 5.05 (dd, J=16, 5.3 Hz, 1H), 5.10 (s, 2H), 6.59 (d, J=7.6 Hz, 1H), 7.12 (s, 1H), 7.20 (d, J=7.6 Hz, 1H), 7.48 (m, 2H), 7.69 (m, 2H), 7.90 (d, J=5.3 Hz, 1H); IR (KBr) 3600–3100, 3100–2800, 1681, 1613, 1601, 1485, 1445, 1314, 830, 764, 742 cm⁻¹; MS (ES) m/e 422 (M+H)⁺. Anal. Calcd for C₂₁H₂₁N₅O₄: C, 61.91: H, 5.20: N, 17.19. Found; C, 61.57; H, 5.32; N, 17.29.

EXAMPLE 8

Preparation of (S)-2,3,4,5-Tetrahydro-7-[[[(4-aza-5-methylbenzimidazol-2-yl)methyl]methylamino]carbonyl]-3-oxo-1H-1,4benzodiazepine-2-acetic acid a) Methyl (S)-2,3,4,5-tetrabydro-7-[[[(4-aza-5-methylbenzimidazol-2-yl)methyl]methylamino]carbonyl]-3-oxo-1H-1,4-benzodiazepine-2-acetate A mixture containing methyl (S)-2,3,4,5-tetrahydro-7-bromo-3-oxo-1H-1,4-benzodiazepine-2-acetate (624 mg, 2 mmol), 2-(aminomethyl)4-aza-5-methylbenzimidazole dihydrochloride (695 mg, 2.8 mmol), DIEA (1.8 mL, 10 mmol), and (Ph₃P)₂PdCl₂ (126 mg, 0.18 mmol) in NMP (22 mL) was heated to 110° C. under a CO balloon for 48 hr. The solvent was removed on the rotavap (high vacuum) and the residue was purified by silica gel flash chromatography (0.5–5% CH₃OH/CH₂Cl₂) to give the title compound (170 mg, 19.5%) as a pale yellow solid: MS (ES) m/e 437.5 (M+H)⁺.

b) (S)-2,3,4,5-Tetrahydro-7-[[[(4-aza-5-methylbenzimidazol-2-yl)methyl]methylamino]carbonyl]-3-oxo-1H-1,4-benzodiazepine-2-acetic acid 1.0 M LiOH (0.6 mL, 0.6 mmol) was added dropwise to a solution of methyl (S)-2,3,4,5-tetrahydro-7-([[(4-aza-5-methylbenzimidazol-2-yl)methyl]methylamino]carbonyl]-3-oxo-1H-1,4-benzodiazepine-2-acetate (170 mg, 0.39 mmol) in $CH_3OH$ (5 mL) and ThF (5 mL) at RT. The resulting mixture was stirred for 20 hr and then was concentrated. The residue was dissolved in $H_2O$, acidified with 30% TFA, and purified by ODS chromatography (5% $CH_3CN/H_2O$ containing 0.1% TFA). Concentration and lyophilization gave the title compound as an off white powder: $[\alpha]_n^{25}$ –74.5° (c 1, $CH_3OH$); MS (ES) m/e 423.2 (M+H)$^+$. Anal. Calcd for $C_{21}H_{22}N_6O_4$.2 TFA.1.75 $H_2O$: C, 44.03; H, 4.06; N, 12.32. Found: C, 44.33; H, 4.04; N, 12.28.

EXAMPLE 9

Preparation of Methyl 2,3,4,5-tetrahydro-7-[[(N'-benzyoxycarbonyl)-4,4'-bipiperidinyl]carbonyl]-3-oxo-4-methyl-1H-1,4-benzodiazepine-2-acetate N-CBZ-4,4'-bipiperidine-HCl salt (1.18 g, 0.0035 mole) was dissolved in hot N-methylpyrrolidone (8 ml) and filtered. To the filtrate was added Hunigs base (3.64 g, 0.028 mole), methyl 2,3,4,5-tetrahydro-7-iodo-3-oxo-1H-1,4-benzodiazepine-2-acetate (1.0 g, 0.0027 mole) and $(Ph_3P)_2PdCl_2$ (0.038 g, 5.4'10$^{-6}$ mole) added. The mixture was degassed and heated at 90–100° C. under one atmosphere of carbon monoxide for 2.0 hours. The reaction was cooled and the product isolated in an identical manner to that described for the preceding Example 6 to yield the title compound (1.38 g, 90%).

EXAMPLE 10

Preparation of 7-[[(1'-benzyloxycarbonyl)-4,4'-bipiperidinyl]carbonyl]-3-oxo-2,3,4,5-tetrahydro-1H-1,4-benzodiazepine-2-acetic acid A slurry of 7-iodo-3-oxo-2,3,4,5-tetrahydro-1,4-benzodiazepine-2-acetic acid (7.2 g, 0.02 mol), 1'-benzyloxycarbonyl-4,4'-bipiperidine hydrochloride (0.026 mol), Hunigs base (0.1 mol) and dichlorobis (triphenylphosphine) palladium (II) (2 mol % in 8 vol anisole) was stirred and heated to 95° C. while bubbling with nitrogen. The mixture was flushed with carbon monoxide, then heated under an atmosphere of carbon monoxide for approximately 2 hours after which palladium black precipitated from solution. Analysis by HPLC demonstrated that reaction was complete. The reaction mixture was cooled to 80° C. and the product was extracted with water (8 vol) at this temperature. After separating, the organic phase was washed with more water (8 vol) and separted. The combined aqueous phases were distilled at atmospheric pressure to remove residual anisole and Hunigs base. The distillation was stopped when no more organic material could be seen to distill. The residual aqueous solution was cooled to room temperature, acidified to pH 2 with 10% hydrochloric acid and the product precipitated from solution as white solid. The product was filtered under suction, washed with water and dried in vacuum oven at 50° C. to afford the title compound as a dark solid (10.2 g, 91%).

EXAMPLE 11

Preparation of methyl (S) 7-[[(N'-benzyloxycarbony)-4,4'-bipi.peridinyl]carbonyl]-3-oxo-2,3,4,5-tetrahydro-1,4-benzodiazepine-2-acetic acid a) methyl 7-[[(N'-benzyloxycarbonyl)-4,4'-bipiperidinyl]carbonyl]-3-oxo-2,3,4,5-tetrahydro-1,4-benzodiazepine-2-acetate A mixture of methyl 7-iodo-3-oxo-2,3,4,5-tetrahydro-1,4-benzodiazepine-2-acetate (50 g, 134 mmol), N'-benzyloxycarbonyl-4,4'-bipiperidine hydrochloride (52.12 g, 154 mmol), Hunigs base (67.9 ml, 402 mmol.), NMP (200 ml), water (5.2 ml, 289 mmol) and palladium II chloride bistriphenylphosphine (1.88 g, 2.68 mmol) was shaken in a Parr shaker at 95° C. under carbon monoxide at 8–14 psi. After 4 h carbon monoxide uptake ceased and the reaction mixture was allowed to cool to room temperature. Dichloromethane (400 ml) was then added and the solution was filtered and washed with water. The organic layer was concentrated to dryness and the residue was slurried in methanol (770 ml). The product was filtered and washed with methanol and sucked dry to afford the title compound (54 g, 70%).

b) (S) 7-(4,4'-bipiperidinyl)carbonyl-3-oxo-2,3,4,5-tetrahydro-1H-1,4-benzodiazepine-2-acetic acid The compound of Example 11(a) was dissolved in t-butanol and buffer (70 ml, pH 7.0, 0.1 N phosphate). *Candida antarctica* lipase, supported on macroporous acrylate resin (200 mg, /700 PLU/g, marketed as Novozym 435) was added and the reaction stirred at ambient temperature for 4.0 days. The pH was adjusted to 8.0 with NaOH solution and EtOAc added (75 ml). The mixture was filtered, and the EtOAc layer separated. The aqueous layer was re-extracted with EtOAc, the combined EtOAc extracts were dried ($Na_2SO_4$) and the EtOAc evaporated in vacuo to yield the (R)-ester.

The aqueous phase was adjusted to pH 5 with HCl and extracted with EtOAc. The combined EtOAc extracts were dried ($Na_2SO_4$) and evaporated to leave the (S) acid (99% e.e.)

A solution of the (S) acid (0.15 mmol) in methanol (40 mL) and acetic acid (8 drops) was shaken in a hydrogen atmosphere (45 psi) with 10% Pd/C (20 mg) for 30 min. The mixture was filtered through Celite and the filtrate concentrated in vacuo to yield the title compound.

EXAMPLE 12

Preparation of (S)-2,3,4,5-Tetrahydro-3-oxo-7-[[[2-[2-(pyridinyl)amino]ethyl]amino]carbonyl]-1H-1,4benzodiazepine-2-acetic acid a) Methyl (S)-2,3,4,5-Tetrahydro-3-oxo-7-[[[2-[2-(pyridinyl)amino]ethyl]amino]carbonyl]-1H-1,4-benzodiazepine-2-acetate A mixture of Methyl (S)-2,3,4,5-Tetrahydro-7-iodo-3-oxo-1H-1,4-benzodiazepine-2-acetate (720 mg, 2 mmol), N-(2-pyridinyl)ethylenediamine (672 mg, 3 mmol), DIEA (1.8 mL, 10 mmol), and $(Ph_3P)_2PdCl_2$ (140 mg, 0.2 mmol) in N-methyl-2-pyrrolidinone (20 mL) was heated to 110° C. under CO balloon for 3 h. The mixture was concentrated and the residue was purified by flash chromatography (silica gel, step bradient, 0–7% $CH_3OH/CH_2Cl_2$) to give the title compound as a pale yellow semisolid: MS (ES) m/e 398.2 [M+H]$^+$.

b) (S)-2,3,4,5-Tetrahydro-3-oxo-7-[[[2-[2-(pyridinyl)amino]ethyl]amino]carbonyl]-1H-1,4-benzodiazepine-2-acetic acid 1M LiOH (3.8 mL, 3.8 mmol) was added dropwise to a solution of the compound of Example 12(a) (1 g, 2.5 mmol) in 1:1 CH$_3$OH:THF (20 mL) at RT. The resulting mixture was stirred for 20 h and concentrated. The residue was dissolved in H$_2$O, acidified with TFA (20%), and purified by chromatography (ODS, 6% CH$_3$CN/H$_2$O-0.1% TFA). Fractions containing the desired product were pooled, concentrated, and lyophilized to give the title compound [may contain approximately 23% of the R-enantiomer, see Preparation 6(c)] as a pale yellow powder: MS (ES) m/e 384.2[M+H]$^+$. Anal. Calcd for C$_{19}$H$_{21}$N$_5$O$_4$.2.5 TFA: C,41.87; H, 3.44; N, 10.17. Found: C, 42.01; H, 3.62; N, 10.15.

EXAMPLE 13

Preparation of (S)-2,3,4,5-Tetrahydro-7-[[[(benzimidazol-2-yl)methyl]amino]carbonyl]-3-oxo-1H-1,4-benzodiazepine-2-acetic acid a) Methyl (S)-2,3,4,5-tetrahydro-7-[[[(benzimidazol-2-yl)methyl]amino]carbonyl]-3-oxo-1H-1,4-benzodiazepine-2-acetate A mixture of methyl (S)-2,3,4,5-tetrahydro-7-ixdo-3-iodo-1H-1,4-benzodiazepine-2-acetate (1.08 g, 3 mmol), 2-aminomethylbenzimidazole dihydrocnchloride hydrate (924 mg, 4.2 mmol), DIEA (2.6 mL, 15 mmol), and (Ph$_3$P)$_2$PdCl$_2$ (211 mg, 0.3 mmol) in NMP (30 mL) was heated to 110° C. under a CO balloon for 3 hr. The solvent was removed on the rotavap (high vacuum) and the residue was purified by silica gel flash chromatography (0–7% CH$_3$OH/CH$_2$Cl$_2$) to afford the title compound (530 mg, 44%) as an off white solid: MS(ES) m/e 408.1 (M+H)$^+$.

b) (S)-2,3,4,5-Tetrahydro-7-[[[(benzimidazol-2-yl)methyl]amino]carbonyl]-3-oxo-1H-1,4-benzodiazepine-2-acetic acid Methyl (S)-2,3,4,5-tetrahydro-7-[[[(benzimidazol-2-yl)methyl]amino]carbonyl]-3-oxo-1H-1,4-benzodiazepine-2-acetate is hydrolyzed with 1M LiOH to yield the title compound (66%) as a white powder: [α]$_n^{25°}$ –145.3° (c=1, CH$_3$OH); MS (ES) m/e 394.2 (M+H)$^+$. Anal. Calcd for C$_{20}$H$_{19}$N$_5$O$_4$.2 TFA.0.125 H$_2$O: C, 46.22; H, 3.43; N, 11.23. Found: C, 46.13; H, 3.78; N, 11.49.

The above description fully discloses how to make and us the present invention. However, the present invention is not limited to the particular embodiments described hereinabove, but includes all modifications thereof within the scope of the following claims. The various references to journals, patents and other publications which are cited herein comprises the state of the art and are incorporated herein by reference as though fully set forth.

What is claimed is:

1. A process for preparing compounds of formula (I):

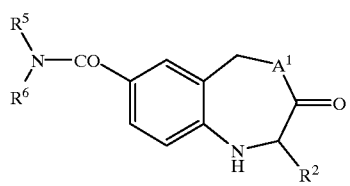
(I)

wherein

A$^1$ is NR$^1$ or CHR$^1$;

R$^1$ is H, T—C$_{1-6}$alkyl, T—C$_{1-6}$oxoalkyl, T—C$_{2-6}$alkenyl, T—C$_{3-4}$oxoalkenyl, T—C$_{3-4}$oxoalkynyl, T—C$_{3-4}$alynyl, C$_{3-6}$cycloalkyl, Ar or Het, optionally subsituted by one or more of halo, —OR', —CN, —NR'$_2$, —NO$_2$, —CF$_3$, —CO$_2$R', —CONR'$_2$, Ar—C$_{0-6}$alkyl or Het-C$_{0-6}$alkyl, wherein T is H, C$_{3-6}$cycloalkyl, Het or Ar, R$^2$ is CH$_2$CO$_2$R$^3$;

R$^3$ is H, C$_{1-6}$alkyl, C$_{3-7}$cycloalkyl-C$_{0-4}$alkyl or Ar—C$_{0-4}$alkyl;

R$^5$ is W—(CR'$_2$)$_q$—Z—(CHR')$_m$, and

R$^6$ is H, C$_{1-6}$alkyl, Ar—C$_{0-6}$alkyl, Het-C$_{0-6}$alkyl, or C$_{3-6}$cycloalkyl-C$_{0-6}$alkyl, or R$^5$ and R$^6$ together form a 5- or six-membered Het ring which is substituted by W, W is R$^9$R"N—, R'R"NR'N—, R'R"NR'NCO—, R'$_2$NR'NC(=NR')—, R'ONR'C(=NR')—,

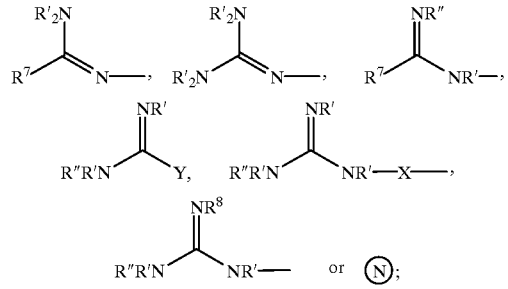

R' is H, C$_{1-6}$alkyl, C$_{3-7}$cycloalkyl-C$_{0-4}$alkyl or Ar—C$_{0-4}$alkyl;

R" is R', —C(O)R' or —C(O)OR'";

R'" is H, C$_{1-6}$alkyl or Ar—C$_{0-4}$alkyl;

R$^7$ is R', —CF$_3$, —SR', or —OR';

R$^8$ is R', C(O)R', CN, NO$_2$, SO$_2$R' or C(O)OR$^{15}$;

R$^9$ is H, C$_{1-6}$alkyl, C$_{3-7}$cycloalkyl-C$_{0-4}$alkyl, Het-C$_{0-4}$alkyl or Ar—C$_{0-4}$alkyl;

X is N=CR', C(O) or O;

Y is absent, S or O;

Z is (CH$_2$)$_t$, Het, Ar or C$_{3-7}$cycloalkyl;

q is 0 to 3;

m is 0 to 2; and t is 0 to 2;

which process comprises:

reacting a compound of formula (II):

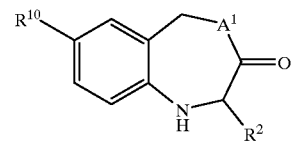
(II)

wherein

A$^1$ and R$^2$ are as defined above for formula (I); and

R$^{10}$ is Br, I, FSO$_3$—, ClSO$_3$— or CF$_3$SO$_3$–;

with a Pd catalyst, carbon monoxide and an amine of the formula (III)

(III)

wherein R$^5$ and R$^6$ are defined as above in formula (I) except that any basic nitrogen group in R$^5$ or R$^6$ is protected, and thereafter removing any protecting groups.

2. A process according to claim 1 wherein the amine of formula (III) is N'-benzyloxycarbonyl-4,4'-bipiperidine or N'-t-butyloxycarbonyl-4,4'-bipiperidine.

3. A process according to claim 1 wherein the palladium catalyst is $(Ph_3P)_2Pd(Cl)_2$.

4. A process according to claim 1 which is conducted in a N-methylpyrrolidinone solvent.

5. A process according to claim 1 wherein $R^{10}$ is I.

6. A process according to claim 1 wherein $R^{10}$ is Br.

7. A process according to claim 6 in which, greater than a 15 mole % of palladium catalyst is used.

8. A process according to claim 6 in which greater than a 15 mole % of triphenyl phosphine is present.

9. A process according to claim 8 which is run in the presence of a reducing agent.

10. A process for preparing the intermediate compound of formula (II):

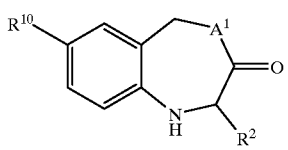
(II)

wherein $R^{10}$ is Br, which comprises reacting a compound of formula (IV):

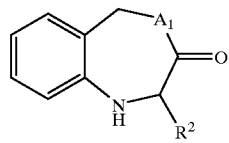
(IV)

wherein $A^1$ and $R^2$ are as defined in claim 1, with N-bromosuccinimide and a tetraalkyl ammonium halide.

11. A process for preparing the intermediate compound of formula (II):

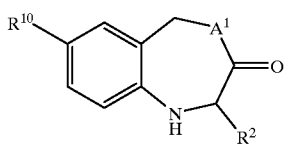
(II)

wherein $R^{10}$ is I, which comprises reacting a compound of formula (IV):

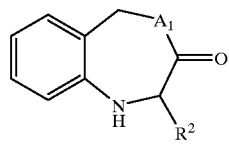
(IV)

wherein $A^1$ and $R^2$ are as defined in claim 1, with ICl.pyridine in a solvent mixture of methylene dichloride and methanol.

12. An intermediate compound of the formula (II) or (IV):

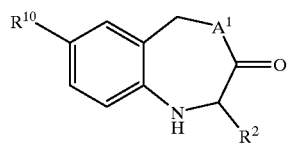
(II)

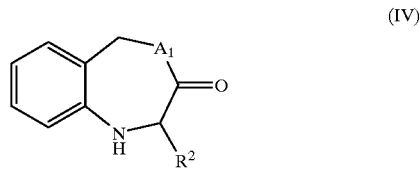
(IV)

wherein $R^{10}$ is $CF_3SO_3$, Br or I, and $A^1$ and $R^2$ are as defined in claim 1.

13. An intermediate compound of formula (IV):

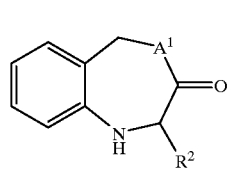
(IV)

wherein $A^1$ and $R^2$ are as defined in claim 1.

14. A compound according to claim 13 which is methyl (S)-2,3,4,5-tetrahydro-3-oxo-1H-1,4-benzodiazepine-2-acetate.

15. A process for preparing a compound according to claim 13, which comprises, reacting dimethyl N-[2-(cyano)phenyl]-aspartate with a reducing agent.

16. A compound which is dimethyl N-[2-(cyano)phenyl]-aspartate.

17. A process for preparing compounds of formula (I):

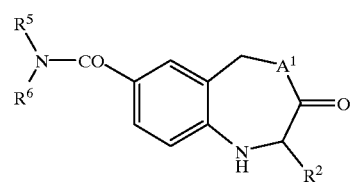
(I)

wherein $A^1$ is $NR^1$ or $CHR^1$;

$R^1$ is H, T—$C_{1-6}$alkyl, T—$C_{1-6}$oxoalkyl, T—$C_{2-6}$alkenyl, T—$C_{3-4}$oxoalkenyl, T—$C_{3-4}$oxoalkynyl, T—$C_{3-4}$alkynyl, $C_{3-6}$cycloalkyl, Ar or Het, optionally substituted by one or more of halo, —OR', —CN, —NR'$_2$, —NO$_2$, —CF$_3$, —CO$_2$R', —CONR'$_2$, Ar—$C_{0-6}$alkyl or Het-$C_{0-6}$alkyl, wherein T is H, $C_{3-6}$cycloalkyl, Het or Ar, $R^2$ is $CH_2CO_2R^3$;

$R^3$ is H, $C_{1-6}$alkyl, $C_{3-7}$cycloalkyl-$C_{0-4}$alkyl or Ar—$C_{0-4}$alkyl;

$R^5$ is W-(CR'$_2$)$_q$-Z-(CHR')$_m$, and $R^6$ is H, $C_{1-6}$alkyl, Ar—$C_{0-6}$alkyl, Het-$C_{0-6}$alkyl, or $C_{3-6}$cycloalkyl-$C_{0-6}$alkyl, or $R^5$ and $R^6$ together form a 5- or six-membered Het ring which is substituted by W;

W is $R^9R''N-$, $R'R''NR'N-$, $R'R''NR'NCO-$, $R'_2NR'NC(=NR')-$, $R'ONR'C(=NR')-$,

[structures shown]

R' is H, $C_{1-6}$alkyl, $C_{3-7}$cycloalkyl-$C_{0-4}$alkyl or Ar—$C_{0-4}$alkyl;
R'' is R', —C(O)R' or —C(O)OR''';
R''' is H, $C_{1-6}$alkyl or Ar—$C_{0-4}$alkyl;
$R^7$ is R', —$CF_3$, —SR', or —OR';
$R^8$ is R', C(O)R', CN, $NO_2$, $SO_2R'$ or $C(O)OR^{15}$;
$R^9$ is H, $C_{1-6}$alkyl, $C_{3-7}$cycloalkyl-$C_{0-4}$alkyl, Het-$C_{0-4}$alkyl or Ar—$C_{0-4}$alkyl;
X is N=CR', C(O) or O;
Y is absent, S or O;
Z is $(CH_2)_t$, Het, Ar or $C_{3-7}$cycloalkyl;
q is 0 to 3;
m is 0 to 2; and
t is 0 to 2;
which process comprises:
converting a compound of formula (IV)

(IV)

to a compound of formula (I).

18. A process for preparing compounds of formula (I):

(I)

wherein
$A^1$ is $NR^1$ or $CHR^1$;
$R^1$ is H, T—$C_{1-6}$alkyl, T—$C_{1-6}$oxoalkyl, T—$C_{2-6}$alkenyl, T—$C_{3-4}$oxoalkenyl, T—$C_{3-4}$oxoalkynyl, T—$C_{3-4}$alkynyl, $C_{3-6}$cycloalkyl, Ar or Het, optionally substituted by one or more of halo, —OR', —CN, —$NR'_2$, —$NO_2$, —$CF_3$, —$CO_2R'$, —$CONR'_2$, Ar—$C_{0-6}$alkyl or Het-$C_{0-6}$alkyl, wherein T is H, $C_{3-6}$cycloalkyl, Het or Ar,
$R^2$ is $CH_2CO_2R^3$;
$R^3$ is H, $C_{1-6}$alkyl, $C_{3-7}$cycloalkyl-$C_{0-4}$alkyl or Ar—$C_{0-4}$alkyl;
$R^5$ is W-$(CR'_2)_q$-Z-$(CHR')_m$, and
$R^6$ is H, $C_{1-6}$alkyl, Ar—$C_{0-6}$alkyl, Het-$C_{0-6}$alkyl, or $C_{3-6}$cycloalkyl-$C_{0-6}$alkyl, or
$R^5$ and $R^6$ together form a 5- or six-membered Het ring which is substituted by W;
W is $R^9R''N-$, $R'R''NR'N-$, $R'R''NR'NCO-$, $R'_2NR'NC(=NR')-$, $R'ONR'C(=NR')-$,

[structures shown]

R' is H, $C_{1-6}$alkyl, $C_{3-7}$cycloalkyl-$C_{0-4}$alkyl or Ar—$C_{0-4}$alkyl;
R'' is R', —C(O)R' or —C(O)OR''';
R''' is H, $C_{1-6}$alkyl or Ar—$C_{0-4}$alkyl;
$R^7$ is R', —$CF_3$, —SR', or —OR';
$R^8$ is R', C(O)R', CN, $NO_2$, $SO_2R'$ or $C(O)OR^{15}$;
$R^9$ is H, $C_{1-6}$alkyl, $C_{3-7}$cycloalkyl-$C_{0-4}$alkyl, Het-$C_{0-4}$alkyl or Ar—$C_{0-4}$alkyl;
X is N=CR', C(O) or O;
Y is absent, S or O;
Z is $(CH_2)_t$, Het, Ar or $C_{3-7}$cycloalkyl;
q is 0 to 3;
m is 0 to 2; and
t is 0 to 2;
which process comprises:
converting dimethyl N-[2-(cyano)phenyl]-asparte to a compound of formula (I).

19. A process according to claim 1 wherein $R^1$ is methyl.

20. A process according to claim 17 wherein $R^3$ is methyl, t-butyl or benzyl.

21. A process according to claim 1 wherein the amine of formula (III) is 4,4'-bipiperidine.

22. A compound of claim 13 in which $A^1$ equals $NCH_3$, and $R^2$ equals —$CH_2CO_2Me$.

* * * * *